United States Patent [19]
Sullivan

[11] Patent Number: 6,058,934
[45] Date of Patent: May 9, 2000

[54] PLANAR HEMATOCRIT SENSOR INCORPORATING A SEVEN-ELECTRODE CONDUCTIVITY MEASUREMENT CELL

[75] Inventor: Kevin J. Sullivan, Medfield, Mass.

[73] Assignee: Chiron Diagnostics Corporation, E. Walpole, Mass.

[21] Appl. No.: 08/739,234

[22] Filed: Oct. 29, 1996

Related U.S. Application Data

[60] Provisional application No. 60/006,173, Nov. 2, 1995.

[51] Int. Cl.[7] .............................. A61B 5/05; G01N 27/02
[52] U.S. Cl. ..................... 128/635; 128/637; 204/409; 204/412; 422/82.02; 436/150; 324/444; 324/446; 324/693; 324/717
[58] Field of Search ..................... 128/635, 632, 128/637; 204/403, 409, 412; 422/82.02; 436/63, 150; 324/439, 444, 446, 693, 713, 715, 717, 71.1

[56] References Cited

U.S. PATENT DOCUMENTS

| | | | |
|---|---|---|---|
| 3,556,950 | 1/1971 | Dahms | 204/1 |
| 3,648,159 | 3/1972 | Stansell et al. | 324/30 R |
| 3,648,160 | 3/1972 | Beaver | 324/30 B |
| 3,657,548 | 4/1972 | Parkin | 250/203 R |
| 3,692,410 | 9/1972 | Jurány et al. | 356/40 |
| 3,699,345 | 10/1972 | Parkin | 250/203 |
| 3,700,905 | 10/1972 | Parkin et al. | 250/203 R |
| 3,702,401 | 11/1972 | Parkin | 250/210 |
| 3,805,601 | 4/1974 | Jeffers | 73/88.5 |
| 3,821,496 | 6/1974 | Malone | 191/12.2 R |
| 3,829,761 | 8/1974 | Shimizu et al. | 324/30 B |
| 3,838,379 | 9/1974 | Gieles et al. | 338/42 |
| 3,891,843 | 6/1975 | Parkin | 250/203 R |
| 3,921,066 | 11/1975 | Angel et al. | 324/71 CP |
| 3,923,397 | 12/1975 | Shuck | 356/39 |
| 3,930,726 | 1/1976 | Dolive | 356/39 |
| 3,956,015 | 5/1976 | Rogers | 136/86 |
| 3,963,979 | 6/1976 | Dauphinee | 324/30 |
| 3,993,945 | 11/1976 | Warmoth et al. | 324/30 B |
| 3,997,420 | 12/1976 | Buzza | 204/195 P |

(List continued on next page.)

OTHER PUBLICATIONS

C. G. Olthof, et al., "Non–Invasive Conductivity Technique to Detect Changes in Haematocrit: in vitro Validation", *Medical and Biological Engineering and Computing*, vol. 32, No. 5 (Sep. 1994) pp. 495–500.

*Primary Examiner*—Jennifer Bahr
*Assistant Examiner*—Eric F. Winakur
*Attorney, Agent, or Firm*—Arthur S. Morgenstern; Gordon R. Moriarty; Robert P. Blackburn

[57] ABSTRACT

A conductivity sensor for measuring hematocrit and a sensor housing for a blood analysis instrument using the conductivity sensor are described. The conductivity sensor includes a seven-electrode conductivity measurement cell in which three symmetric pairs of electrodes are arranged on opposite sides of a central electrode. The central electrode is connected to an AC source and the outermost pair of electrodes, which provide a return path for the current, are maintained at a ground or reference potential. The two inner pairs of electrodes measure the voltage drop along the current flow path. This arrangement confines the measurement current and potential within the sensor chamber, thereby preventing the sensor from interfering with other electrochemical sensors that may be provided in the blood analysis instrument. The sensor housing provides a linear arrangement of flow cells defining a fluid flow path through the housing. The conductivity and other sensors are each located within an associated cell to form a wall portion of the flow path. The housing arrangement is simple to assemble and provides a flow path which resists fouling and is readily flushed out.

16 Claims, 7 Drawing Sheets

U.S. PATENT DOCUMENTS

| | | | |
|---|---|---|---|
| 3,997,838 | 12/1976 | Shamos et al. | 324/71 R |
| 4,015,199 | 3/1977 | Rommel | 324/30 B |
| 4,063,309 | 12/1977 | Hennessy et al. | 364/555 |
| 4,068,169 | 1/1978 | Angel et al. | 324/71 CP |
| 4,092,232 | 5/1978 | Zetter | 204/195 P |
| 4,096,047 | 6/1978 | Hale et al. | 204/195 P |
| 4,118,663 | 10/1978 | Barben, II et al. | 324/30 R |
| 4,187,462 | 2/1980 | Haker et al. | 324/204 |
| 4,198,474 | 4/1980 | Shah | 429/6 |
| 4,202,747 | 5/1980 | Buzza et al. | 204/195 R |
| 4,227,987 | 10/1980 | Kircher et al. | 204/228 |
| 4,261,345 | 4/1981 | Yamaguchi | 128/6 |
| 4,301,412 | 11/1981 | Hill et al. | 324/442 |
| 4,303,887 | 12/1981 | Hill et al. | 324/441 |
| 4,340,565 | 7/1982 | Kitajima et al. | 422/56 |
| 4,362,994 | 12/1982 | Goldsmith et al | 324/449 |
| 4,365,200 | 12/1982 | Goldsmith | 324/449 |
| 4,369,656 | 1/1983 | Ueno et al. | 73/204 |
| 4,411,866 | 10/1983 | Kanno | 422/25 |
| 4,452,682 | 6/1984 | Takata et al. | 204/403 |
| 4,469,593 | 9/1984 | Ishihara et al. | 210/96.2 |
| 4,484,135 | 11/1984 | Ishihara et al. | 324/71.1 |
| 4,513,248 | 4/1985 | Miller | 324/439 |
| 4,547,735 | 10/1985 | Kiesewetter et al. | 324/450 |
| 4,632,485 | 12/1986 | Brown et al. | 339/75 M |
| 4,651,121 | 3/1987 | Furubayashi et al. | 338/35 |
| 4,656,427 | 4/1987 | Dauphinee | 324/444 |
| 4,658,651 | 4/1987 | Le | 73/708 |
| 4,686,479 | 8/1987 | Young et al. | 324/439 |
| 4,710,550 | 12/1987 | Kranbuehl | 526/60 |
| 4,723,908 | 2/1988 | Kranbuehl | 432/37 |
| 4,743,352 | 5/1988 | Watkins-Pitchford | 204/406 |
| 4,751,466 | 6/1988 | Colvin et al. | 324/449 |
| 4,761,764 | 8/1988 | Watanabe | 365/181 |
| 4,835,477 | 5/1989 | Polaschegg et al. | 324/439 |
| 4,899,759 | 2/1990 | Pederson et al. | 128/693 |
| 4,944,748 | 7/1990 | Bramm et al. | 623/3 |
| 4,972,137 | 11/1990 | Dunstan et al. | 324/71.4 |
| 4,990,457 | 2/1991 | Tanaka et al. | 436/171 |
| 5,025,219 | 6/1991 | Gaspard | 324/447 |
| 5,078,741 | 1/1992 | Bramm et al. | 623/3 |
| 5,096,505 | 3/1992 | Fraas et al. | 136/246 |
| 5,097,841 | 3/1992 | Moriuchi et al. | 128/675 |
| 5,100,554 | 3/1992 | Polaschegg | 210/647 |
| 5,105,820 | 4/1992 | Moriuchi et al. | 128/675 |
| 5,112,455 | 5/1992 | Cozzette et al. | 204/153.12 |
| 5,118,361 | 6/1992 | Fraas et al. | 136/246 |
| 5,182,947 | 2/1993 | Fidelak et al. | 73/304 C |
| 5,200,345 | 4/1993 | Young | 436/63 |
| 5,230,341 | 7/1993 | Polaschegg | 128/668 |
| 5,275,171 | 1/1994 | Barcel | 607/122 |
| 5,296,752 | 3/1994 | Groeneveld et al. | 307/353 |
| 5,326,344 | 7/1994 | Bramm et al. | 623/3 |
| 5,330,634 | 7/1994 | Wong et al. | 204/409 |
| 5,372,782 | 12/1994 | Karkantis et al. | 422/63 |
| 5,385,581 | 1/1995 | Bramm et al. | 623/3 |
| 5,385,846 | 1/1995 | Kuhn et al. | 436/70 |
| 5,391,499 | 2/1995 | Karkantis et al. | 436/180 |
| 5,416,027 | 5/1995 | Baudin et al. | 436/70 |

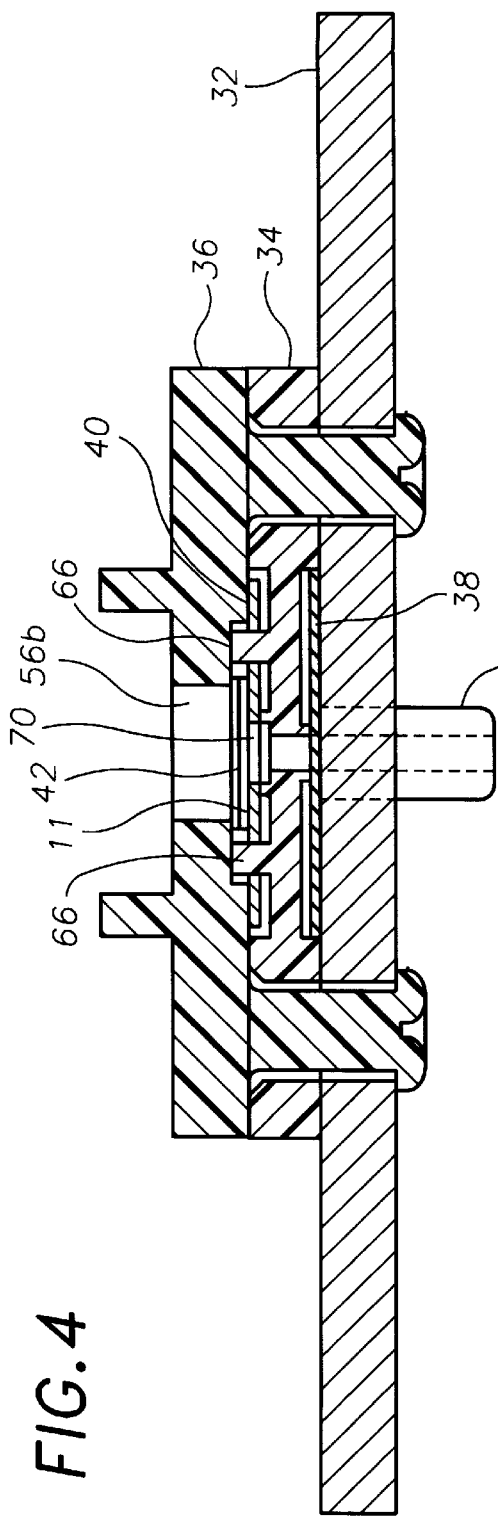
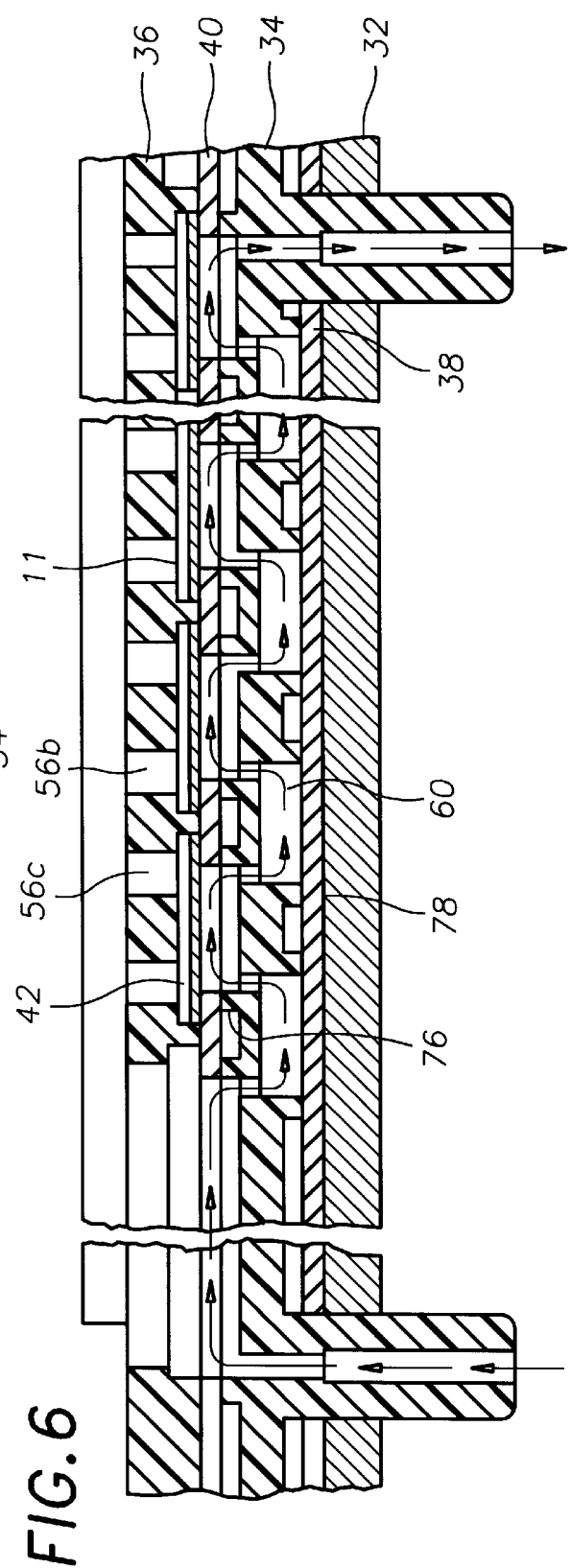
FIG. 4
FIG. 6

US 6,058,934

PLANAR HEMATOCRIT SENSOR INCORPORATING A SEVEN-ELECTRODE CONDUCTIVITY MEASUREMENT CELL

This application claims the benefit of U.S. Provisional Ser. No. 60/006,173 filed Nov. 2, 1995.

FIELD OF THE INVENTION

This invention relates to measuring the conductivity of fluids and more particularly to blood analysis instruments for measuring blood hematocrit.

BACKGROUND OF THE INVENTION

Whole blood hematocrit is a measurement of the volume fraction of the corpuscular components in a blood sample. Hematocrit can be estimated from a measurement of the conductivity of a sample of blood, since blood plasm is a relatively good conductor of electricity, while the blood cells are relative insulators. Various instruments have been developed which incorporate conductivity cells through which a blood sample is flowed to measure the conductivity.

A type of conductivity measurement, known as a four terminal or Kelvin connection, comprises a pair of current carrying electrodes spaced on either side of a pair of voltage measuring electrodes. This technique, in which the voltage measuring electrodes are separated from the current carrying electrodes, enables only a low current to be drawn from the sample, thereby having a negligible effect on the path of the constant current flowing between the current carrying electrodes.

SUMMARY OF THE INVENTION

The present invention provides a conductivity sensor having a stable and predictable response which can be used in a blood analysis instrument to produce an accurate estimate of hematocrit from a minimal sample size and without interfering with other sensors typically used in a blood analysis instrument. The conductivity sensor comprises seven conductive electrodes arranged as three symmetric parallel pairs on either side of a central electrode on an insulating substrate. The central electrode and the two outer electrodes are the current carrying electrodes. The outer electrodes are maintained at a ground or reference potential of the instrument. The remaining four electrodes, connected in parallel in pairs on either side of the central electrode, are the voltage measuring electrodes and are connected to a differential amplifier whose output is a voltage inversely proportional to the conductivity of the sample. This arrangement confines the measurement current to the sensor chamber, preventing the conductivity sensor from interfering with other sensors in the blood analysis instrument. The conductivity sensor can be provided on a chip in a small size.

The present invention also provides a sensor housing in which the conductivity sensor may be retained along with other sensors typically used in a blood analysis instrument. The sensor housing has a generally planar configuration, thereby simplifying the manufacturing process and permitting efficient fluidics so that the cells can be filled and washed out with minimal reagent volumes. The housing comprises a base plate and flow cell plate providing a linear arrangement of flow cells along a flow path, each flow cell having a receptacle to receive a sensor chip, such as the conductivity sensor of the present invention. The base plate and flow cell plate are attached to a heater plate which maintains the fluid at an appropriate temperature. Gaskets between the base plate and flow cell plate and between the flow cell plate and the heater plate further define and seal the flow path. The linear arrangement of the flow cells within the housing provides a flow path which resists fouling and washes out efficiently.

DESCRIPTION OF THE DRAWINGS

The invention will be more fully understood from the following detailed description taken in conjunction with the accompanying drawings in which:

FIG. 4 is a cross-sectional side view of the sensor housing and heater plate of FIG. 1 in the assembled configuration;

FIG. 6 is a partial cross-sectional front view of the sensor housing and heater plate of FIG. 1 an the assembled configuration illustrating the fluid flow path therethrough;

DETAILED DESCRIPTION OF THE INVENTION

Figure 1:
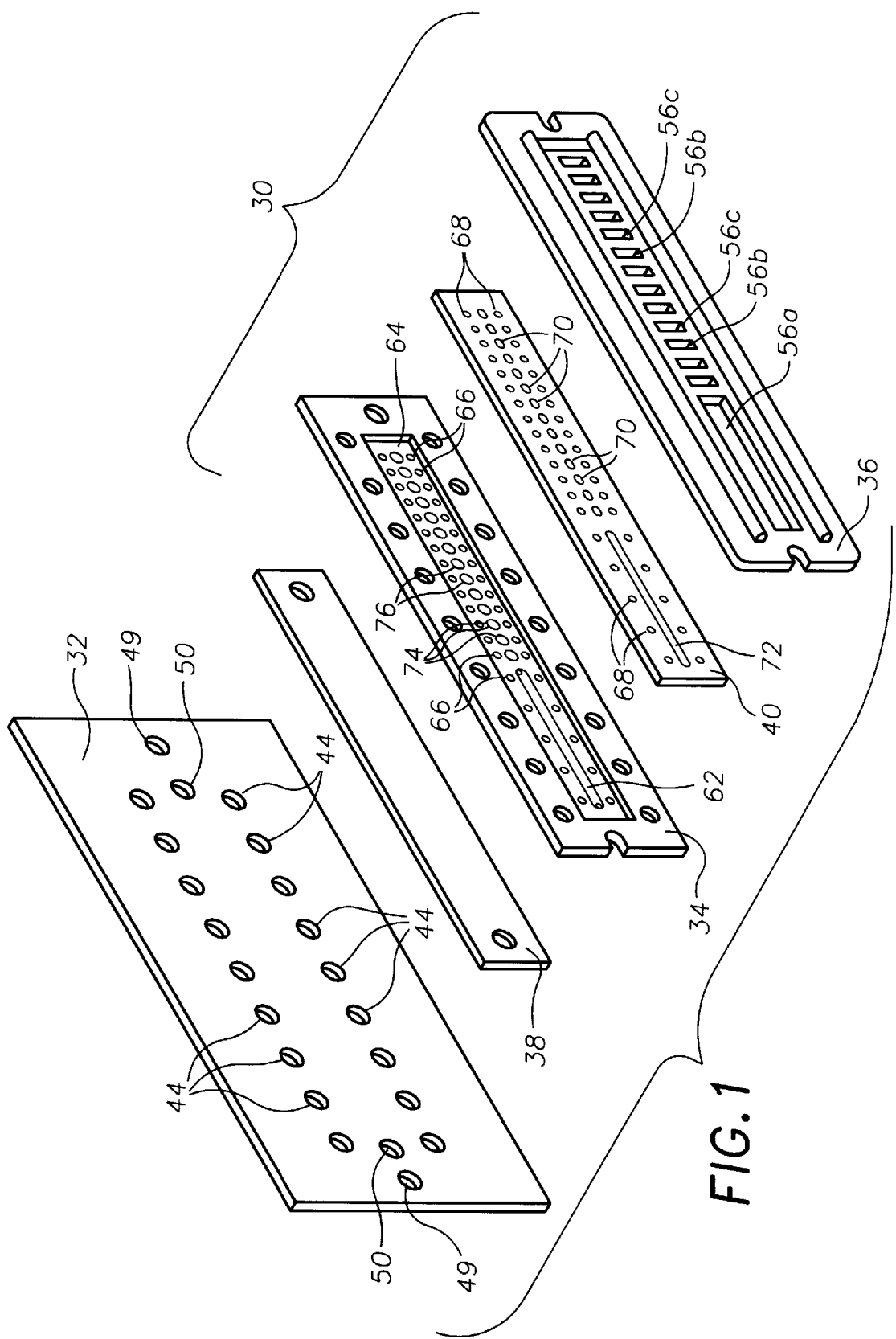
FIG. 1 is an exploded perspective view of a sensor housing and heater plate for use in a blood analysis device according to the present invention.
Figure 2:
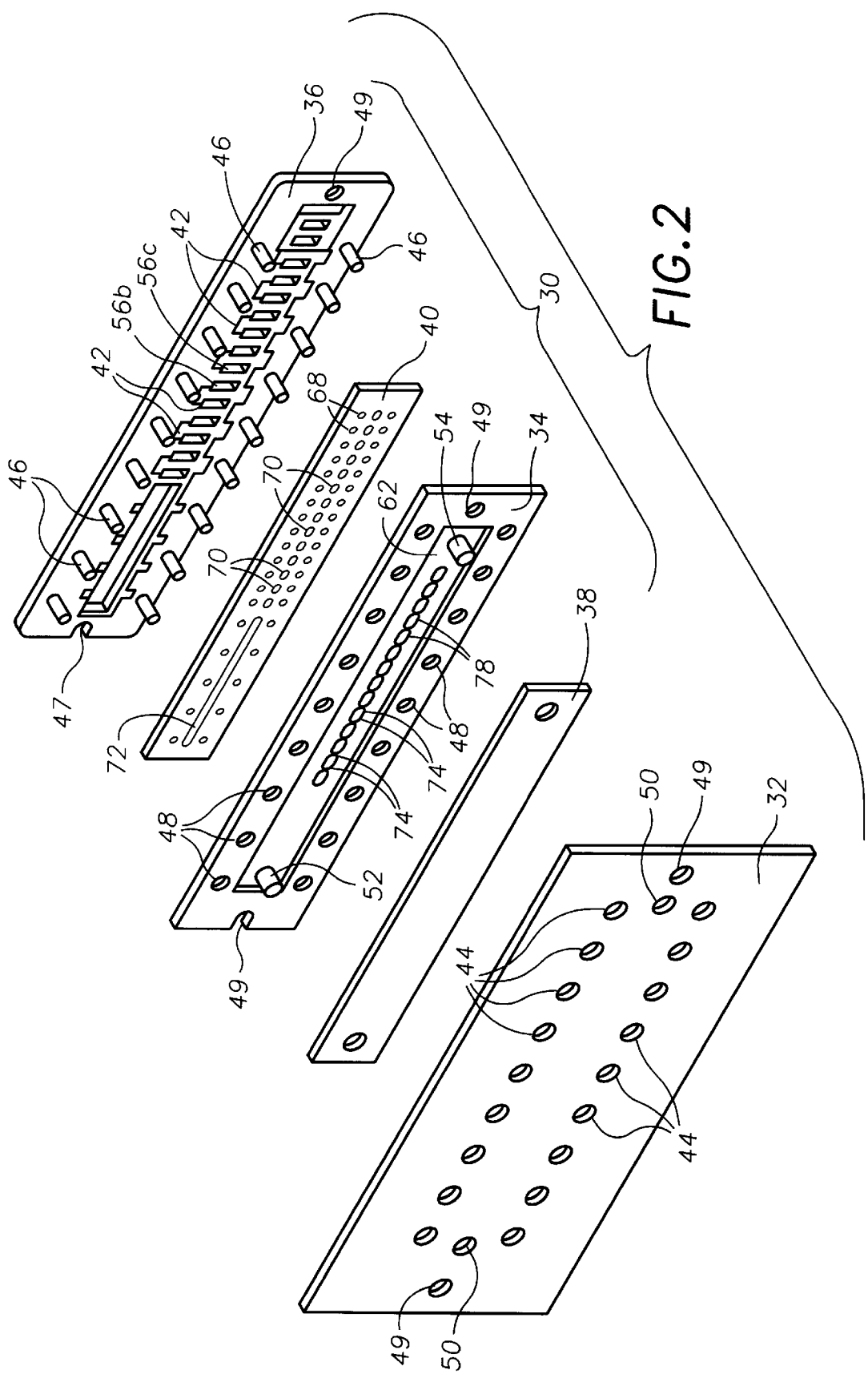
FIG. 2 is a further exploded perspective view of the sensor housing and heater plate of FIG. 1 illustrating opposite sides thereof.
Figure 3:
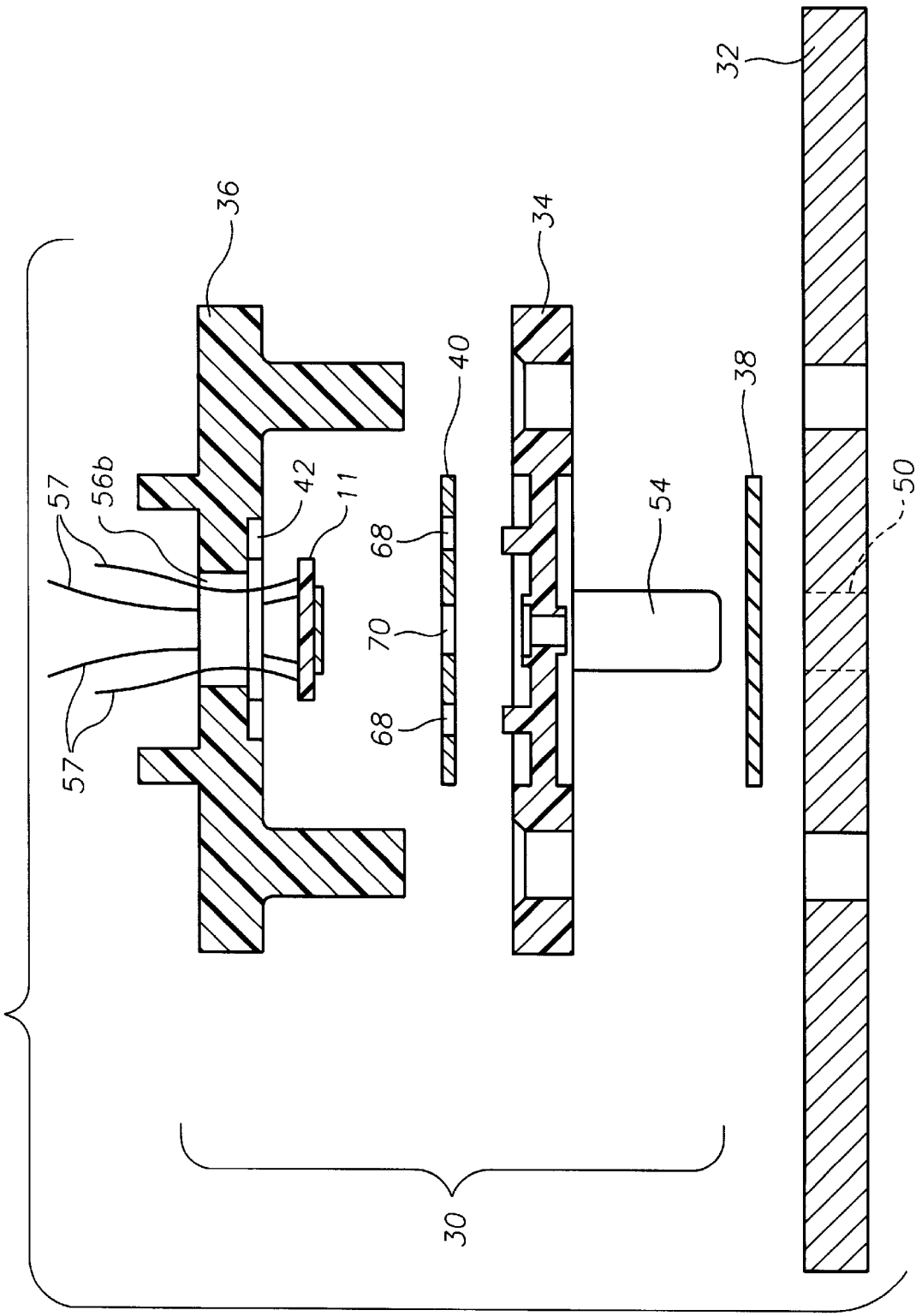
FIG. 3 is an exploded cross-sectional side view of the sensor housing and heater plate of FIG. 1.
Figure 5:
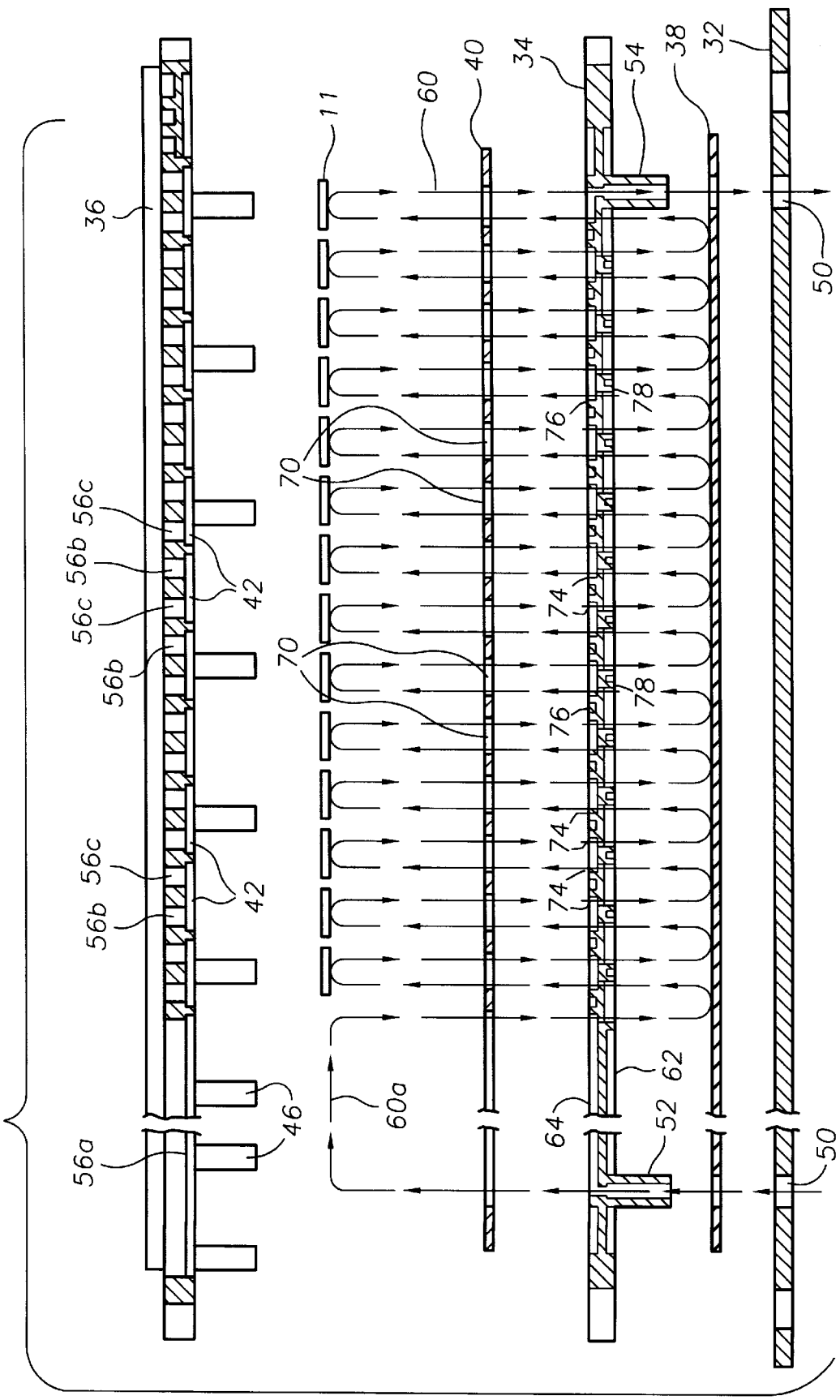
FIG. 5 is an exploded cross-sectional front view of the sensor housing and heater plate of FIG. 1 illustrating the fluid flow path therethrough.
Figure 7:
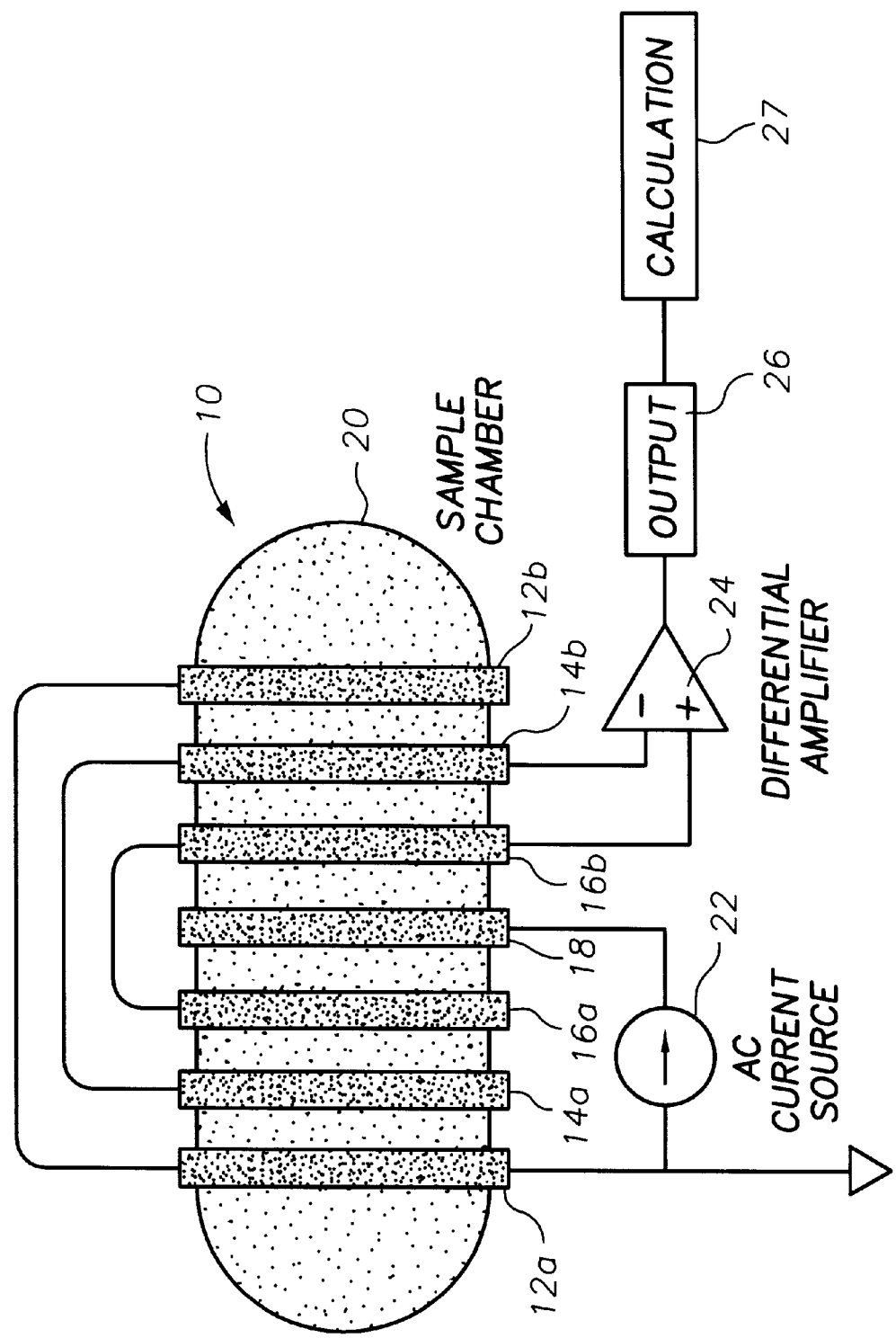
FIG. 7 is a schematic illustration of a planar conductivity sensor according to the invention.
Figure 8:
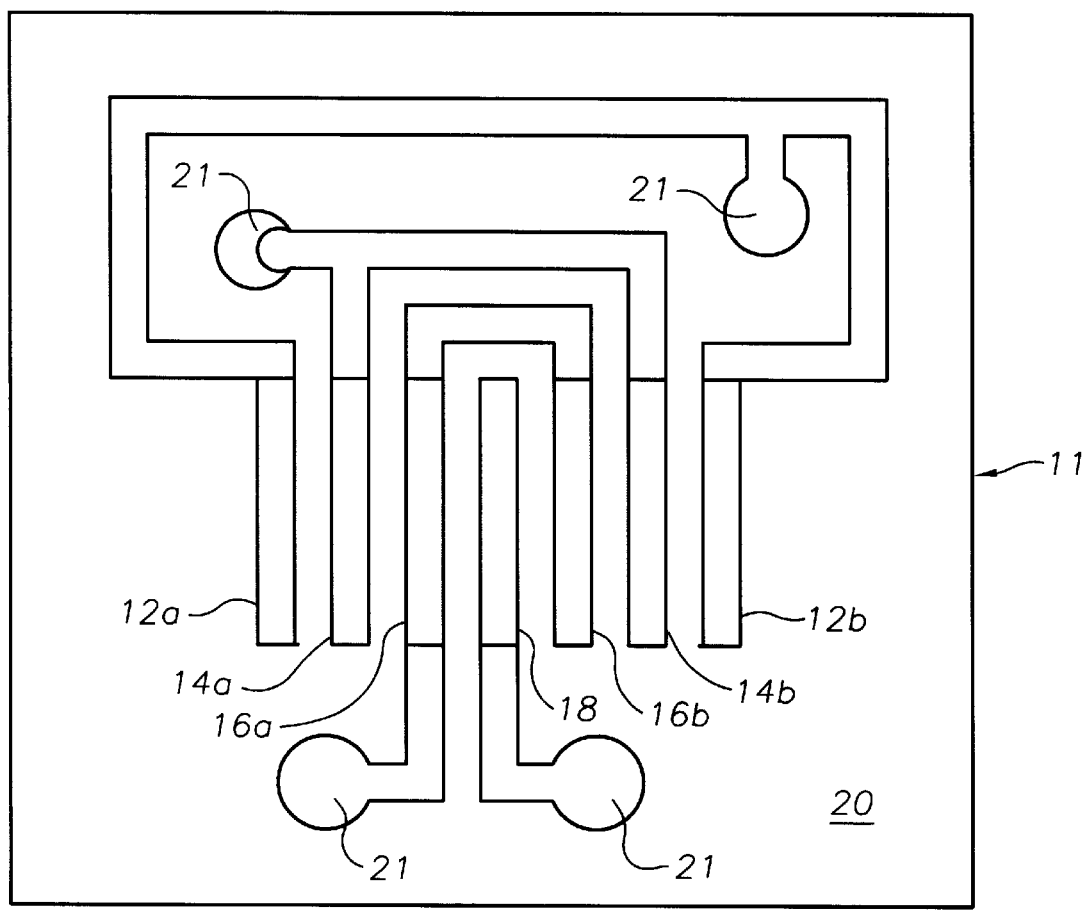
FIG. 8 is a plan view of the electrodes of the conductivity sensor of FIG. 7 formed on a chip.

A conductivity sensor 10 according to the present invention is shown in FIG. 7. The sensor comprises seven electrodes 12a, 12b, 14a, 14b, 16a, 16b, 18 arranged in a parallel array on a planar substrate 20. Any suitable conductive material, such as gold, silver, platinum, or stainless steel, can be used for the electrodes, and any suitable insulating material, such as alumina, glass, or G-10 epoxy, can be used for the substrate. For use as a hematocrit sensor in a blood analysis apparatus, the electrodes are laid down as parallel metal strips on the substrate. The electrodes, including contact pads 21, and substrate, are formed as a small chip 11, illustrated in FIG. 8. The size of the chip 11 may be, for example, approximately 0.12 by 0.12 inches. The chip can be disposed in a flow cell receptacle in a sensor housing, described in more detail below, to form one wall of a fluid flow path on which fluid flows perpendicularly to the parallel arrangement of the electrodes. Other electrode configurations, such as annular rings disposed on the interior of a tubular substrate, may be used, depending on the application.

The seven conductive electrodes are arranged as three symmetric parallel pairs 12a and 12b, 14a and 14b, and 16a and 16b, on either side of the central electrode 18. The central electrode 18 is connected to a source 22 of alternating current to maintain an approximately constant rms alternating current between the central electrode 18 and the outermost pair of electrodes 12a, 12b. The outermost pair of electrodes are maintained at the reference or ground potential of the instrument in which the conductivity sensor is incorporated. Holding the outer electrodes at a reference potential confines the measurement current to the sensor chamber, preventing the conductivity sensor from interfering with other electrochemical sensors that may be in contact with the blood sample.

The two inner pairs of electrodes 14a, 14b, 16a, 16b, between the central electrode 18 and the outer electrodes 12a, 12b, are electrically connected in parallel and sense the potential drop along a portion of the current path. The symmetrical arrangement of the current source electrodes makes this voltage drop equal in each direction from the central electrode. The signal from the voltage measuring electrodes is processed by a differential amplifier 24, whose output 26 is a voltage whose RMS amplitude is inversely proportional to conductivity.

The calculation of conductivity requires knowledge of current flow, potential drop, and the geometry of the current path. The translation from conductivity to hematocrit is made using known relationships. A suitable processor-based circuit 27 is provided to perform the calculations and otherwise process and display the result.

The combination of this arrangement of multiple electrodes and sensing electronics allows a low current to be drawn from the sample by the measuring instrumentation, having a negligible effect on the path of the constant current flowing between the central and outer electrodes, while controlling the current path through the sample to eliminate interference with other adjacent sensors. The width and spacing of the electrodes are not critical, typically both being 0.005 inches, and preferably produce an electrical field that penetrates the depth of the sample chamber in which the sensor is located and has a uniform gradient in that portion of the potential field that is measured by the voltage sensing electrodes 14a, 14b, 16a, 16b. Keeping the high gradient areas around the current carrying electrodes 12a, 12b away from the voltage measuring electrodes 14a, 14b, 16a, 16b greatly reduces the effects of small changes in electrode geometry and electrochemical reactions on the current carrying electrode surfaces.

Referring to FIGS. 1 through 6, the sensor 10 is used in a blood analysis device which has a sensor housing 30 disposed on a heater plate 32. The sensor housing comprises a flow cell plate 34 laid adjacent to the heater plate 32 and a base plate 36 laid over the flow cell plate 34. A crossover gasket 38 is disposed between the flow cell plate 34 and the heater plate 32. A sensor gasket 40 is disposed between the flow cell plate 34 and the base plate 36. The conductivity sensor 10 in the form of the small chip 11 described above is laid in one of a series of flow cell receptacles 42 formed in the base plate 36, discussed further below. The strip electrodes are arranged to lie perpendicularly to the direction of fluid flow on the flow path.

The heater plate 32 is in a heat exchange relationship with the sensor housing 30 to maintain the sensor housing and the fluid flow therethrough at an appropriate temperature. The heater plate is generally planar and extends beyond the edges of the sensor housing. The heater plate is formed of a material having a good heat conductivity, as is known in the art. For example, a metal such as aluminum has been found suitable. The heater plate is maintained at the appropriate temperature in any suitable manner, as is also known in the art.

A first array of openings 44, generally arranged along two lines, is formed through the heater plate. The first array of openings receive retaining pins 46 formed on the base plate 36. The retaining pins fit through corresponding openings 48 formed in the flow cell plate 34 and aid in holding the flow cell and base plate in contact with the heater plate along the length of the housing to ensure good heat transfer from the heater plate to the housing. The pins are swaged by ultrasonic energy to hold the plates together. The sensor housing is fastened to the heater plate in any suitable manner, such is by a pair of screws and nuts (not shown) which are received in aligned openings 49 formed through the base plate, flow cell plate, and heater plate at each end thereof.

A further pair of openings 50 through the heater plate receive flow input and output pins 52, 54 which extend from the flow cell plate 34. Preferably, the input and output pins are integrally formed with the flow cell plate. The input and output pins are hollow to define flow channels therethrough through which fluids enter and exit the sensor housing, discussed further below.

The base plate 36 comprises an elongated planar member having a series of apertures 56a, 56b, 56c extending along a central longitudinal axis. A first aperture 56a is elongated to provide a flow path on which the temperature of the fluid can equalize with the temperature of the housing. The remaining apertures are provided in pairs 56b, 56c, each pair associated with a chip receiving receptacle 42. Each receptacle 42 is formed by a recess in the base plate surrounding each pair of apertures. The conductivity sensor chip 11 described above rests in one receptacle 42. The other receptacles receive various other types of sensors, as are known in the blood analysis art. The apertures 56b, 56c allow communication with the sensors via leads 57 which attach to the contact pads 21. For example, electrical connection to the electrodes of the conductivity sensor is made through its associated apertures. The elongated aperture 56a also includes a surrounding recess.

The flow cell plate 34 also comprises an elongated planar member and defines a flow path therealong indicated by arrow 60 between the crossover gasket 38 and the sensor gasket 40. An elongated recess 62 is formed in the underside of the flow cell plate, the side adjacent the heater plate in the assembled condition. The crossover gasket 38 is retained in the elongated recess. A further elongated recess 64 is formed on the opposite side of the flow cell plate, the side adjacent the base plate. The sensor gasket 40 is retained in the further elongated recess. A plurality of nubs 66 extend from the flow cell plate to fit within corresponding apertures 68 in the sensor gasket to aid in retention of the sensor gasket to the flow cell plate. The sensor gasket also includes a plurality of flow path defining apertures 70 which correspond to and align with the sensor chips retained in the receptacles 42 such that a portion of each sensor chip forms a portion of the wall of the flow path 60. An elongated aperture 72 is also provided in the sensor gasket which aligns with the elongated aperture 56a of the base plate.

A plurality of apertures 74 extend along the central longitudinal axis of the flow cell plate 34 to form part of the flow path 60. The flow path is further defined by upraised rings 76, 78 surrounding pairs of the apertures on each side of the flow cell plate. The upraised rings seal against the sensor gasket 40 and the crossover gasket 38 respectively to provide a flow path between apertures of a pair. The rings 76 on one side of the plate are offset from the rings 78 on the other side of the plate to provide a flow path that alternates from one side of the plate to the other. The rings 76 on the side adjacent the base plate and sensor gasket form a portion of the wall of each flow cell chamber. The apertures 74 at each end of the flow cell plate communicate with the input and output flow channels formed in the input and output pins 52, 54.

In operation, the desired sensor chips are laid in associated receptacles 42 in the base plate 36, and the sensor housing 30 is assembled. Fluid enters the housing through the input channel in the pin 52 and flows along the elongated section 60a of the flow path 60. As the fluid flows along this section, the fluid's temperature is equalized to the temperature of the housing. The fluid may be a sample of blood to be analyzed, a calibration or reference fluid, or a wash solution to clean out the flow path. The fluid continues flowing along the flow path, alternating from one side to the other of the flow cell plate 34, and exits the housing at the output channel in the pin 54. As it flows through the housing 30, the fluid flows past and directly contacts each sensor in its associated receptacle while flowing on the side of the flow cell plate 34 adjacent the base plate 36. In this manner, the flow cells are linearly aligned and the flow path deviates minimally from a straight line. With this configuration, the size of a blood sample may be minimal, for example, 150 μl. Fouling of the flow path is minimized and the flow path may be readily washed out.

The sensor housing 30 is formed of any suitable insulating material, such as polycarbonate. The housing may be manufactured relatively simply in any suitable manner. For example, the flow cell plate and the base plate may be formed by injection molding. The gaskets may be formed by molding. The housing is readily assembled.

The invention is not to be limited by what has been particularly shown and described, except as indicated by the appended claims.

We claim:

1. A fluid conductivity measuring sensor comprising:
   a substrate comprising an insulating material adapted to define a flow path across the substrate surface when the substrate is installed in a cell of a fluid flow system;
   seven electrodes disposed in parallel alignment on the substrate, the electrodes comprising:
      a central electrode adapted to be in electrical communication with a source of current when the substrate is installed in the cell of the fluid flow system,
      an outermost pair of electrodes symmetrically spaced on either side of the central electrode and adapted to be electrically connected as a return current path to the current source at a reference potential when the substrate is installed in the cell of the fluid flow system;
      a first pair and a second pair of voltage measuring electrodes disposed symmetrically on opposite sides of the central electrode, the first pair and the second pair adapted to be electrically connected in parallel to instrumentation to measure the potential difference across each of the pairs of voltage measuring electrodes when the substrate is installed in the cell of the fluid flow system.

2. The fluid conductivity measuring sensor of claim 1, further comprising a differential amplifier in electrical communication with the voltage measuring electrodes to measure the potential difference across each of the pairs of voltage measuring electrodes.

3. The fluid conductivity measuring sensor of claim 1, wherein the electrodes comprise metal strips deposited on the substrate.

4. The fluid conductivity measuring sensor of claim 3, wherein the metal strips are formed of gold.

5. The fluid conductivity measuring sensor of claim 1, wherein the substrate comprises a planar element.

6. The fluid conductivity measuring sensor of claim 1, wherein the central electrode and the outermost pair of electrodes are in electrical communication with a source of a constant rms alternating current.

7. The fluid conductivity measuring sensor of claim 1, wherein the substrate and the seven electrodes are formed as a chip.

8. The fluid conductivity measuring sensor of claim 7, wherein said chip is approximately 0.12 by 0.12 inches.

9. The fluid conductivity measuring sensor of claim 1, wherein said electrodes have a width of approximately 0.005 inches.

10. The fluid conductivity measuring sensor of claim 1, wherein said electrodes are spaced apart approximately 0.005 inches.

11. A blood analysis system comprising:
    an elongated housing having a longitudinally extending axis, a flow path formed through the housing and extending generally along the longitudinally extending axis, a plurality of flow cells linearly arranged along the flow path, each flow cell having a sensor receiving receptacle formed in a wall thereof; and
    a hematocrit sensor formed as a chip disposed in an associated sensor receiving receptacle within the housing, the hematocrit sensor comprising:
       a planar substrate comprising an insulating material adapted to define a flow path across the substrate surface;
       seven electrodes disposed in parallel alignment on the substrate, the electrodes comprising:
          a central electrode adapted to be in electrical communication with a source of current,
          an outermost pair of electrodes symmetrically spaced on either side of the central electrode and adapted to be electrically connected as a return current path to the current source at a reference potential;
          a first pair and a second pair of voltage measuring electrodes disposed symmetrically on opposite sides of the central electrode, the first pair and the second pair adapted to be electrically connected in parallel to instrumentation to measure the potential difference across each of the pairs of voltage measuring electrodes;
    the chip disposed in the sensor receiving receptacle with the seven electrodes arranged perpendicularly to the flow path.

12. The blood analysis system of claim 11, further comprising a differential amplifier in electrical communication with the voltage measuring electrodes to measure the potential difference across each of the pairs of voltage measuring electrodes.

13. The blood analysis system of claim 11, wherein the central electrode and the outermost pair of electrodes are in electrical communication with a source of a constant rms alternating current.

14. The blood analysis system of claim 11, wherein said electrodes have a width of 0.005 inch.

15. The blood analysis system of claim 11, wherein said electrodes are spaced apart 0.005 inch.

16. The blood analysis system of claim 11, wherein the elongated housing comprises a planar member having a sensor side and a crossover side, the flow path being formed through the elongated housing from an input channel to an output channel, the flow path defined by apertures formed along a line in the planar member to provide fluid communication between the sensor side and the crossover side, the flow path further defined by sealed flow cells disposed along a line on the sensor side of the planar member and located between adjacent pairs of apertures, the flow path further defined by sealing members disposed along a line on the crossover side of the planar member to provide sealed flow path portions between adjacent pairs of apertures, each sealed flow path portion on the crossover side of the planar member being offset from each flow cell on the sensor side of the planar member, whereby the flow path alternates between the sensor side and the crossover side.

* * * * *